United States Patent [19]

Maoka et al.

[11] Patent Number: 5,859,224
[45] Date of Patent: Jan. 12, 1999

[54] BASE SEQUENCE OF THE COAT PROTEIN GENE OF PAPAYA LEAF-DISTORTION MOSAIC VIRUS

[75] Inventors: Tetsuo Maoka, Okinawa; Satoshi Kashiwazaki, Ibaraki; Tomio Usugi, Okinawa; Hiroyuki Hibino, Ibaraki, all of Japan

[73] Assignee: Japan International Research Center for Agricultural Sciences, Ministry of Agriculture, Forestry and Fisheries, Ibaraki, Japan

[21] Appl. No.: 609,503

[22] Filed: Mar. 1, 1996

[30] Foreign Application Priority Data

Mar. 24, 1995 [JP] Japan ..................................... 7-066501

[51] Int. Cl.$^6$ ........................... C12N 15/11; C12N 15/13; C07H 21/00
[52] U.S. Cl. ...................... 536/23.72; 435/69.1; 435/440
[58] Field of Search ........................ 536/23.72; 800/205, 800/DIG. 64, DIG. 73; 435/69.1, 172.3, 418, 419

[56] References Cited

PUBLICATIONS

Matzke and Matzke. Plant Physiol. 1995. vol. 107: 679–685, 1995.

Finnegan and McElory. Bio/Technology. 1994. vol. 12: 883–888, 1994.

Carvalho et al. The EMBO Journal. 1992. vol. 11: 5995–5602), 1992.

Nejidat et al. Physiologia plantarum. 1990. vol. 80; 662–668, 1990.

Napoli et al. 1989. The plant Cell. vol. 2: 279–289.

Maoka, T., et al. "Nucleotide Sequence of the 3' Terminal Region of Papaya Leaf–Distortion Mosaic Potyvirus RNA", (Meeting of the 80th Anniversary of The Phytopathological Society of Japan, Preliminary Papers, Mar. 30–Apr. 2, 1995 at Setagaya Campus, Tokyo University of Agriculture), copy of Japanese original with English translation attached.

*Primary Examiner*—Elizabeth F. McElwain
*Assistant Examiner*—Ousama M-Faiz Zaghmout
*Attorney, Agent, or Firm*—Davidson, Davidson & Kappel, LLC

[57] ABSTRACT

The present invention discloses a genomic RNA of papaya leaf-distortion mosaic virus (PLDMV) having the base sequence shown in SEQ ID NO: 1 and a DNA complementary to the above RNA having the base sequence shown in SEQ ID NO: 2. These RNA and cDNA are able to render a plant a resisitance to pLDMV and thus extremely useful industrially.

2 Claims, 1 Drawing Sheet

```
   1  CUCAAUACUUGAGUGGAUAGAAGUAAAACCAGAACACAGAUUAGAAGGCGAUUGCGCUUGCGAUGAGUUGCCUAGGGUUAUCCUAGUUAAUCCAGAAAUUUAU
   1   S I L E W D R S V K P E H R L E A I C A S M I E A W G Y P R L I H E I R K F Y
 119  GCUUGGGUCUGGAACAAGCACCAUACAAUCUCGCACUCGAGGGAAAGCACCAUUUCGGAAGACAGGCGCUCAAAAGACUUUACACAUCCGAAGAAGCUGAUGAAAUC
  40   A W V L E Q A P Y N H L A S E G K A P Y I S E T A L K R L Y T C E E G S A D E I
 239  AUGCAUACUUAGACAGAGUGUGCAAGUGAUUUGAACGAGGACUGUCUUCCUCACCAGUCCCCUCUUGACGCUCGGCAAACCACACCAGAAAACAAGAAAGAC
  80   M S Y L E M C A S D L N E D E Y F D D E D V S H Q/S A L D A G K P T A E N K K D
 359  GAUCAAGAGAAGAAAUAAGCAGGAAAUAAAACCAGGAAAAUAAAAAGAAGUCGACAAGAAACAUGAGAAUAUCGGAAUACCGCAUCUGGUGCUAUUGGUUUCAAACAACGAA
 120   D E E R K N K E E K Q E N K N K N K E V E K K H E K T S N S A S G A I V S N N E
 479  AAAGACAAGGAUGUCGAUGUAGGAUCAAGUGGAUCUUUCAACUGGGAUCUUUCACGGAAUACCACCGAAUAUAAUCGAUAUCCAAAAUGCCAAAAUGGAAUUUUAAAUUGGAGUUC
 160   K D K D V G S S G S F I I P R I K S I S N K L T M P K V K G K I L N L E F
 599  CUUUACAAUACACACCAGAAUGGACAAUUCAAAUACCAGGGCAAGACAUUUAAUAUACAUGGUACAACCGCUGAAGGAAUCCUAUGGUGCUAUCCUGUGAAGGAAUCCUAUGGUGUCUGAUGAAGAAUGGAA
 200   L L Q Y T P D Q V D I S N T R A S I S Q F N T W Y N A V K E S Y G V S D E E M G
 719  AUAAUUUGAAUGGAUUAUGGAUUUGUGCUAUUGGAAAACAUCUCCAAACAAUUAUGGCAUGUGCAAGGGAAGAACAAAAUCGAACCCCCUUCAACCAAUAGUG
 240   I I L N G L M V W C I E N G T S P N I N G M W F M M Q G E E Q I E Y P L Q P I V
 839  GAAAACGCCAAAACCCACUUUGCCUCAGAGUAUUGCCUCGAUAUGGCCUGAGUUGCUGAAGAACAUCGAAAAGAUAAUGAGCAUAUGCCGAGGUACGGUAUUCAACGAAC
 280   E N A K P T L R Q I M A H F S N V A E A Y I E K R N Y E K P Y M P R Y G I Q R N
 959  CUCACCGACAUGAGUUUGGCGCGAUAUGCCGAUAUUUCUAUGAAAUGACGUCGCCACAACCGCCGCACACCAGAGAAGCGCUGGCCCAGAUGAAACCUGCAGCACAGCGAGAUGCCGAAU
 320   L T D M S L A R Y A F D F Y E M T S R T P A R A R E A H I Q M K A A A L R D A N
1079  AAUUAAGAUGUUGGACUGGACUGGAUGGAAAAGUCGGAAAAUGCCGAAAUGCGGACUGAGACAACGGACGAGCCGCACGACCAUGAUAACCAUACACCUCACCGGCCGUUCCGCAUUAUUAGAUA
 360   N K M F G L D G K V G N A T E N T E R H T A D D V N H N T H A F T G V R Y Y*
1199  UUUACCUAAGCAUAGUUUAUCUAGAGCUUUAAAUCGCAUUAAAGUAGGUUUCAGCGCGUUAGGUGUAGGUUUUACCUUCCAUUAUCUAGUCAGUGAGGUAGGGAUGUCAGCCCUCGUGUCA
1319  UCUCUUAGAAAGUAUUGCUCCAAGCUGCCUGCGUGUUCAUAGCCAGUGGCCUCAGCCUUCAGCCUUCAGGCCUUCAGCCUUCAGCCUUCAGCCUUCAGCCUUCAGCCUUCAGCCUUCAGCCUUCAGCCUUCAGCCUUCAGCCUUCAGCCUUCAGCCUUCAGCC
```

FIG. 1   Base Sequence of the Coat Protein Gene of Papaya Leaf-Distortion Mosaic Virus (PLDMV)
(Mark "/" represents the digestion site of NIb and the coat protein and mark "*" represents stop codon.)

5,859,224

BASE SEQUENCE OF THE COAT PROTEIN GENE OF PAPAYA LEAF-DISTORTION MOSAIC VIRUS

BACKGROUND OF THE INVENTION

1. Field of the Invention

The present invention relates to a genomic RNA of papaya leaf-distortion mosaic virus (hereinafter referred to as "PLDMV"), a DNA complementary to the RNA and a method for creating a plant resistant to PLDMV comprising incorporating the above DNA into the genomic DNA of a plant.

2. Prior Art

In papaya growing in the subtropical region of Japan, there occurs a disease called papaya leaf-distortion mosaic wherein leaves bear mosaic symptoms and fruit bears ring spots, and this disease has become a problem. It has been proved that this disease is caused by the infection of PLDMV. In virus classification, PLDMV belongs to the same group as potato virus Y belongs to (the Potyvirus group). It has a flexuous rod shape and a length of about 800 nm. This virus is non-persistently transmitted by aphids. The constituent elements of this virus comprises RNA as the entity of genes and a coat protein surrounding the RNA. The genomic RNA of this virus includes a region which codes for the coat protein.

There has been no finding about this region of the PLDMV genomic RNA nor any report of the base sequence of this region.

Tennant et al. have reported that by introducing into a plant the coat protein gene of the P strain of papaya ring spot virus (PRSV-P), it is possible to render the plant a resistance to PRSV-P [Tennant et al., Phytopathology 84:1359–1366 (1994)]. Accordingly, it is expected that a PLDMV resistant plant could also be created by introducing the coat protein gene of this virus into a plant.

OBJECTS AND SUMMARY OF THE INVENTION

It is the object of the invention to isolate from PLDMV the cDNA coding for its coat protein region and thereby to create a PLDMV resistant plant.

As a result of extensive and intensive researches to solve the above assignment, the present inventors have succeeded in cloning the cDNA coding for the coat protein region. The present invention has been thus achieved.

The present invention relates to a papaya leaf-distortion mosaic virus genomic RNA having the base sequence shown in SEQ ID NO: 1.

The present invention also relates to a DNA complementary to the above papaya leaf-distortion mosaic virus genomic RNA, which DNA has the base sequence shown in SEQ ID NO: 2.

The present invention further relates to a method for creating a plant resistant to papaya leaf-distortion mosaic virus, which method comprises incorporating the DNA described above into the genomic DNA of a plant.

BRIEF DESCRIPTION OF THE DRAWINGS

FIG. 1 shows the base sequence and the amino acid sequence of the PLDMV coat protein gene.

DETAILED DESCRIPTION OF THE INVENTION

Hereinbelow, the present invention will be described in detail.

(1) Cloning of the cDNA Coding for the PLDMV Coat Protein

The cloning of the cDNA coding for the PLDMV coat protein is performed by preparing appropriate primers based on the base sequence information shown in SEQ ID NO: 2 and screening the cDNA library obtained from the virus RNA with the primers. Alternatively, the cDNA coding for the PLDMV coat protein can be obtained directly from the virus RNA by a reverse transcription PCR. A reverse transcription PCR can be carried out, for example, as follows. As Vunsh et al. performed using bean yellow mosaic virus (BYMV) [Vunsh R. et al., Ann. Appl. Biol. 117:561–569 (1990)], two primers are prepared which sandwich the region of interest in the gene sequence. Then, using a commercial reverse transcription PCR kit (Takara Shuzo) and a thermal cycler (Perkin Elmer) and according to the protocol of the above kit, cDNA is synthesized from RNA. By amplifying the resultant cDNA further, the cloning of the cDNA is performed.

When the information of SEQ ID NO: 2 is not used, the cloning can be performed by the following method which the present inventors have employed or by appropriately modifying this method.

First, virions are separated from a PLDMV-infected plant and purified. The separation and purification of virions can be carried out by the method described in the Example. However, means for such separation and purification is not particularly limited to that method. According to that method, the virus can be separated from tuno-nigauri (*Cucumis metuliferus*) and cucumber (*Cucumis sativus*).

Subsequently, RNA is extracted from the separated PLDMV and purified. The RNA can be extracted by those methods conventionally used in the extraction of Potyvirus RNA. After the RNA extraction, the RNA is purified. Since the genomic RNA of PLDMV has poly(A), this purification can be performed by using a column wherein oligo-dT is bound to a carrier.

By using purified A⁺ RNA as a template, double-stranded cDNA is synthesized. Since the genomic RNA of PLDMV has poly(A) as described above, the cDNA of PLDMV can be synthesized by using oligo-dT primers. The synthesized cDNA is inserted into an appropriate vector. Examples of useful vectors for this purpose include pBluescript II (Stratagene), M13 (Toyobo), pUC (Toyobo) and pBR32 (Toyobo). The operation of insertion into a vector can be performed by using a commercial ligation kit.

The resultant vector is introduced into *E. coli* to prepare a cDNA library of PLDMV. The screening of the cDNA library is carried out by culturing the transformed *E. coli* cells separately, extracting plasmids therefrom and examining whether these plasmids hybridize with the RNA of PLDMV.

From the selected transformant, the cDNA is cut out and the base sequence thereof is determined by conventional base sequence determination methods, such as dideoxy method.

(2) Characteristics of the PLDMV Coat Protein Gene and a DNA Complementary thereto (cDNA)

The base sequence of the PLDMV coat protein gene is as shown in SEQ ID NO: 1.

The base sequence of a DNA complementary to the above gene (cDNA) is as shown in SEQ ID NO: 2. The base sequence of this cDNA has 1404 bp. At its 3' end, there are found a poly(A) sequence and an untranslated region consisting of 209 bases following the poly(A) sequence. In the upstream of this region, there is found an open reading frame (ORF) which terminates at the stop codon TAG located at position 1193 from the 5' end. However, the start codon is not found within this sequence and expected to exist still upstream. Out of the 397 amino acids translated from the ORF, 293 amino acids are the coat protein and thus it is clear that this cDNA includes the region coding for the PLDMV coat protein.

The vector E. coli JM109-PL50 into which the above cDNA had been inserted was deposited at the National Institute of Bioscience and Human-technology, Agency of Industrial Science and Technology under the Accession No. FERM BP-5049 (date of deposit: Mar. 22, 1995).

The amino acid sequence (FIG. 1) for this coat protein of which the base sequence has been determined was compared to amino acid sequences of coat proteins from several viruses belonging to the Potyvirus group, such as papaya ring spot virus (PRSV) [Yeh, S. D. et al., J. Ben. Virol. 73:2531–2541, (1992); Quemada H. et al., J. Gen. Virol. 71:203–210 (1990); Bateson, M. and Dale, J. Arch. Virol. 123:101–109 (1992)], potato virus Y (PVY) [Robaglia, C. et al., J. Gen. Virol 70:935–947 (1989)] and soybean mosaic virus (SMV) [Jayaram, C. et al., J. Gen. Virol 73:2067–2077 (1992)]. As a result, the homology to these viruses was so low as 49–59%.

(3) The Utility of the cDNA Coding for the PLDMV Coat Protein

By incorporating the cDNA of the present invention into the genomic DNA of a plant, it is possible to render the plant a resistance to PLDMV. Since the damage of useful plants caused by PLDMV has become very great, the cDNA of the present invention is extremely useful.

(4) Method for Creating a PLDMV-Resistant Plant

The creation of a PLDMV-resistant plant can be performed, in principle, according to the document of Tennant et al., supra. Briefly, a marker gene (such as the kanamycin resistant gene), a promoter sequence for effectively expressing a gene of interest in a plant and the like are added to the gene of interest to be introduced and the gene is incorporated in a plasmid vector. Thereafter, a plant is transformed with the vector through *Agrobacterium tumefaciens*.

PREFERRED EMBODIMENTS OF THE INVENTION

The prevent invention will be described in more detail below with reference to the following Example. Unless otherwise indicated, operational procedures were as described in the book titled "KUROHNINGU TO SHIIKUENSU (Cloning and Sequence)" (I. Watanabe, 1989, Nohson Bunka Co., Ltd.).

EXAMPLE 1

Cloning of the cDNA Coding for the PLDMV Coat Protein Gene (1) Separation and Purification of the Virus To 140 g of PLDMV-inoculated *Cucumis metuliferus*, 450 ml of 0.5M citrate buffer containing 0.56 g of sodium sulfite (adjusted to pH 7.0 with 0.5M citric acid) was added and ground in a blender. The resultant solution was filtered through a double gauze. To the filtrate, carbon tetrachloride was added to give a concentration of 6% based on the total volume and mixed violently. Then, the mixture was centrifuged at 6000 g for 15 minutes at 4° C. to thereby obtain the supernatant. To 500 ml of the supernatant, 37.6 g of polyethylene glycol 6,000, 292 g of sodium chloride and 10 ml of polyethylene glycol mono-p-isooctyl phenyl ether were added and agitated for 90 minutes at 4° C. Then, the resultant mixture was centrifuged at 6000 g for 15 minutes at 4° C. After the centrifugation, 0.1M citrate buffer containing 0.01M sodium sulfite (adjusted to pH 7.0 with 0.1M citric acid; hereinafter referred to as "CD buffer") was added to the precipitated pellet to resuspend it. The suspension was centrifuged at 6000 g for 15 minutes at 4° C. to thereby obtain the supernatant. Thirty milliliters of this supernatant is layered over 3 ml of 40% sucrose solution (prepared with CD buffer) and centrifuged at 125,000 g for 90 minutes. The resultant pellet was resuspended in 20 ml of CD buffer and the suspension was centrifuged at 6,000 g for 15 minutes at 4° C. to thereby obtain the supernatant. Ten milliliters of this supernatant was layered over 2 ml of 40% sucrose solution (prepared with CD buffer) and centrifuged at 125,000 g for 90 minutes. The resultant pellet was resuspended in 2.5 ml of CD buffer and the suspension was centrifuged at 6,000 g for 15 minutes at 4° C. to thereby obtain the supernatant. This supernatant was subjected to cesium sulfate equilibrium density-gradient centrifugation (10–41%, using Hitachi RPS40T rotor, at 38,000 rpm, for 15 hours, at 6° C.). The virus fraction forming a white band was collected and, after dilution with CD buffer, centrifuged at 238,000 g for 90 minutes at 4° C. The virus pellet precipitated was resuspended in 0.3 ml of 0.01M citrate buffer (pH 7.0) to thereby obtain a purified virus standard.

(2) Preparation of PLDMV-RNA

To the purified PLDMV described above, 40 $\mu$l of 50 mM magnesium sulfate and 60 $\mu$l of DNaseI (Boehringer Mannheim) were added and mixed. The purified PLDMV was treated for 1 hour at room temperature to thereby remove contaminant DNAs. Then, the resultant solution was layered over an equal volume of 40% sucrose solution (prepared with 0.01M citrate buffer) and centrifuged at 128,000 g for 60 minutes at 4° C. The precipitated pellet was resuspended in 400 $\mu$l of TE (10 mM Tris-HCl pH 8.0, 1 mM EDTA). To the resultant suspension, 8 $\mu$l of 25% SDS and 16 $\mu$l of Proteinase K (25 mg/ml solution) were added and incubated at 37° C. for 20 minutes. Then, 400 $\mu$l of TE-saturated phenol solution was added thereto and shaken. The resultant solution was centrifuged in an Eppendorf small-sized centrifuge for 5 minutes and the aqueous layer was taken out. After a similar phenol extraction operation was repeated again, 400 $\mu$l of chloroform was added to the aqueous layer and shaken. Then, the resultant solution was centrifuged in an Eppendorf small-sized centrifuge for 5 minutes and the aqueous layer was taken out. After a similar chloroform extraction operation was repeated again, 800 $\mu$l of ether was added to the aqueous layer to thereby carry out phenol extraction. After this phenol extraction was performed two times, 20 $\mu$l of 3M sodium acetate solution (pH 6) and 800 $\mu$l of ethanol were added to the resultant aqueous layer and retained at −80° C. for 20 minutes. Then, the solution was centrifuged in an Eppendorf small-sized centrifuge for 5 minutes to thereby obtain RNA as precipitate. This RNA was dissolved in 50 $\mu$l of distilled water. Poly A$^+$ RNA was purified from the extracted RNA using oligo-dT cellulose (Type 7, Pharmacia) by the method of Nakazato and Edmonds [Nakazato, H. and Edmonds M. Methods in Enzymology 29:431–443 (1974)].

(3) Preparation and Screening of cDNA Library

Since the RNA of those viruses belonging to the Potyvirus group has a poly(A) sequence at 3' end, double-stranded cDNAs were synthesized by using oligo-dT primers. A series of these operations were carried out utilizing a commercial cDNA synthesis kit (Pharmacia) and according to the protocol attached to the kit. The synthesized cDNA was inserted into the SmaI site of the phagemid vector pBluescript II (Stratagene). This reaction was carried out using a ligation kit (Takara Shuzo) and according to the protocol attached to the kit. The reaction products were transformed into *E. coli* JM109.

From the cDNA library of PLDMV thus obtained, small amounts of plasmids were rapidly prepared to thereby obtain clones having inserts. From these clones, a clone (PL50) having an insert of about 1.4 Kb which hybridizes with PLDMV-RNA was obtained by northern blotting. The northern blotting was carried out using ECL direct nucleic acid labelling and detection systems (Amersham) and according to the protocol attached to the kit.

The base sequence of this cDNA was determined according to conventional methods using dideoxy method and analyzed with DNASIS (Ver. 7.0) manufactured by Hitachi Soft Engineering. The base sequence is as shown in SEQ ID NO: 2.

EFFECT OF THE INVENTION

The present invention provides a genomic RNA of PLDMV and a DNA complementary to the RNA. These RNA and cDNA are able to render a plant a resistance to pLDMV and thus extremely useful industrially.

What is claimed is:

1. An isolated genomic RNA of a papaya leaf-distortion mosaic virus having the base sequence shown in SEQ ID NO: 1.

2. A DNA complementary to the isolated genomic RNA of a papaya leaf-distortion mosaic virus of claim 1, which has the base sequence shown in SEQ ID NO: 2.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1404 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 1:

```
CUCAAUACUU  GAGUGGGAUA  GAAGUGUAAA  ACCAGAACAC  AGAUUAGAAG  CGAUUUGCGC    60
UUCGAUGAUU  GAAGCAUGGG  GUUACCCUAG  GUUAAUCCAC  GAAAUUCGAA  AAUUUUAUGC   120
UUGGGUUCUG  GAACAAGCAC  CAUACAAUCA  UCUCGCAUCU  GAGGGAAAGG  CACCAUACAU   180
UUCGGAAACA  GCGCUCAAAA  GACUUUACAC  AUGCGAAGAA  GGAAGUGCUG  AUGAAAUCAU   240
GUCAUACUUA  GAGAUGUGUG  CAAGUGAUUU  GAACGAGGAU  GAGUACUUUG  AUGAUGAAGA   300
UGUUUCUCAC  CAGUCCGCUC  UUGAUGCUGG  CAAACCCACA  GCAGAAAACA  AGAAAGACGA   360
UGAAGAGAGA  AAGAAUAAAG  AAGAAAAGCA  GGAAAAUAAA  AACAAAAAUA  AAGAAGUCGA   420
GAAGAAACAU  GAGAAAACUU  CGAAUAGCGC  AUCUGGUGCU  AUUGUUUCAA  ACAACGAAAA   480
AGACAAGGAU  GUCGAUGUAG  GAUCAAGUGG  AUCUUUCAUC  AUACCACGAA  UUAAAUCGAU   540
AUCCAAUAAA  CUCACAAUGC  CAAAAGUGAA  AGGGAAAGGA  AUUUUAAAUU  GGAGUUCCU   600
UUUACAAUAC  ACACCAGAUC  AAGUGGACAU  UUCAAAUACC  AGGGCAAGUA  UUUCACAGUU   660
UAAUACAUGG  UACAACGCUG  UGAAGGAAUC  CUAUGGUGUG  UCUGAUGAAG  AAAUGGGAAU   720
AAUUUUGAAU  GGAUUAAUGG  UUUGGUGUAU  UGAAAAUGGA  ACAUCUCCAA  ACAUUAAUGG   780
CAUGUGGUUU  AUGAUGCAAG  GGGAAGAACA  AAUCGAAUAC  CCCCUUCAAC  CAAUAGUGGA   840
AAACGCAAAA  CCCACUUUGC  GUCAGAUUAU  GGCUCACUUU  AGCAAUGUUG  CUGAAGCAUA   900
CAUCGAAAAG  AGAAAUUAUG  AGAAGCCAUA  UAUGCCGAGG  UACGGUAUUC  AACGGAACCU   960
CACCGACAUG  AGUUGGCGC   GAUAUGCUUU  UGAUUUCUAU  GAAAUGACAU  CAAGGACGCC  1020
AGCUCGGGCC  CGGGAAGCCC  ACAUCCAGAU  GAAAGCUGCA  GCAUUGCGAG  AUGCGAAUAA  1080
UAAGAUGUUU  GGACUGGAUG  GAAAAGUCGG  AAAUGCGACU  GAGAACACGG  AGCGCCACAC  1140
CGCAGACGAU  GUUAACCAUA  ACACUCAUGC  AUUCACCGGC  GUUCGAUAUU  AUUAGAUAUU  1200
UACCUAAGCA  UAGUUUUAUC  UAGUAUCUUU  UAAAUCGCAU  UAGCUUUACU  UUCUAGCACG  1260
```

-continued

```
CGUUAGUGAG GUUUUACCUC CUAUUAUCUA UGUGUCAGUG AGGGUAGCCC UCGUGUGAUC   1320

UCUUAGAAAG UAUUGUCCCA AGCUGCAGUG GCUGGUUGUU CAUAGCAUGA GUGGCUCAUG   1380

GACCUUCAGC CUAAGCAAGG AGGG                                          1404
```

( 2 ) INFORMATION FOR SEQ ID NO: 2:

( i ) SEQUENCE CHARACTERISTICS:
( A ) LENGTH: 1404 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO: 2:

```
CTCAATACTT GAGTGGGATA GAAGTGTAAA ACCAGAACAC AGATTAGAAG CGATTTGCGC     60

TTCGATGATT GAAGCATGGG GTTACCCTAG GTTAATCCAC GAAATTCGAA AATTTTATGC    120

TTGGGTTCTG GAACAAGCAC CATACAATCA TCTCGCATCT GAGGGAAAGG CACCATACAT    180

TTCGGAAACA GCGCTCAAAA GACTTTACAC ATGCGAAGAA GGAAGTGCTG ATGAAATCAT    240

GTCATACTTA GAGATGTGTG CAAGTGATTT GAACGAGGAT GAGTACTTTG ATGATGAAGA    300

TGTTTCTCAC CAGTCCGCTC TTGATGCTGG CAAACCCACA GCAGAAAACA AGAAAGACGA    360

TGAAGAGAGA AAGAATAAAG AAGAAAAGCA GGAAAATAAA AACAAAAATA AAGAAGTCGA    420

GAAGAAACAT GAGAAAACTT CGAATAGCGC ATCTGGTGCT ATTGTTTCAA ACAACGAAAA    480

AGACAAGGAT GTCGATGTAG GATCAAGTGG ATCTTTCATC ATACCACGAA TTAAATCGAT    540

ATCCAATAAA CTCACAATGC CAAAAGTGAA AGGGAAAGGA ATTTTAAATT TGGAGTTCCT    600

TTTACAATAC ACACCAGATC AAGTGGACAT TTCAAATACC AGGGCAAGTA TTTCACAGTT    660

TAATACATGG TACAACGCTG TGAAGGAATC CTATGGTGTG TCTGATGAAG AAATGGGAAT    720

AATTTTGAAT GGATTAATGG TTTGGTGTAT TGAAAATGGA ACATCTCCAA ACATTAATGG    780

CATGTGGTTT ATGATGCAAG GGGAAGAACA AATCGAATAC CCCCTTCAAC CAATAGTGGA    840

AAACGCAAAA CCCACTTTGC GTCAGATTAT GGCTCACTTT AGCAATGTTG CTGAAGCATA    900

CATCGAAAAG AGAAATTATG AGAAGCCATA TATGCCGAGG TACGGTATTC AACGGAACCT    960

CACCGACATG AGTTTGGCGC GATATGCTTT TGATTTCTAT GAAATGACAT CAAGGACGCC   1020

AGCTCGGGCC CGGGAAGCCC ACATCCAGAT GAAAGCTGCA GCATTGCGAG ATGCGAATAA   1080

TAAGATGTTT GGACTGGATG GAAAAGTCGG AAATGCGACT GAGAACACGG AGCGCCACAC   1140

CGCAGACGAT GTTAACCATA ACACTCATGC ATTCACCGGC GTTCGATATT ATTAGATATT   1200

TACCTAAGCA TAGTTTTATC TAGTATCTTT TAAATCGCAT TAGCTTTACT TTCTAGCACG   1260

CGTTAGTGAG GTTTTACCTC CTATTATCTA TGTGTCAGTG AGGGTAGCCC TCGTGTGATC   1320

TCTTAGAAAG TATTGTCCCA AGCTGCAGTG GCTGGTTGTT CATAGCATGA GTGGCTCATG   1380

GACCTTCAGC CTAAGCAAGG AGGG                                          1404
```